(12) United States Patent
Mishima (10) Patent No.: US 6,468,256 B1
(45) Date of Patent: *Oct. 22, 2002

(54) ARTICLE FOR DISPOSAL OF BODY WASTES

(75) Inventor: Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,138

(22) Filed: May 10, 2000

(30) Foreign Application Priority Data

May 10, 1999 (JP) .......................... 11-128894

(51) Int. Cl.[7] ............................... A61F 13/15
(52) U.S. Cl. ................. 604/385.14; 604/385.23; 604/395; 604/385.26; 604/385.29; 604/385.19; 604/385.03; 604/385.09; 604/385.01
(58) Field of Search ............... 604/385.14, 385.01, 604/385.23, 395, 385.26

(56) References Cited

U.S. PATENT DOCUMENTS 4,590,931 A    5/1986   Kidwell, Jr.
5,304,159 A  * 4/1994   Tanji et al. ............. 604/358
5,439,459 A  * 8/1995   Tanji et al. ............. 156/164
6,168,583 B1 * 1/2001   Tanji ................... 604/385.14

FOREIGN PATENT DOCUMENTS

JP    6-178795    6/1994
WO    86/06621    11/1986
WO    98/48753    11/1998

* cited by examiner

Primary Examiner—Rodney M. Lindsey
Assistant Examiner—Angela J Grayson
(74) Attorney, Agent, or Firm—Lowe Hauptman Gilman & Berner, LLP (57) ABSTRACT

An article for disposal of body wastes includes a liquid-pervious inner sheet, a liquid-impervious outer sheet and a liquid-absorbent core disposed therebetween; tapered front and rear end sections and a pair of intermediate sections extending therebetween; and a bottom, a peripheral wall consisting of a front peripheral wall portion with its pointed front end, a rear peripheral wall portion with a pointed rear end and a pair of intermediate peripheral wall portions spaced from each other so that a distance therebetween gradually decreases toward the front and rear peripheral wall portions, respectively.

9 Claims, 8 Drawing Sheets

ARTICLE FOR DISPOSAL OF BODY WASTES

BACKGROUND OF THE INVENTION

This invention relates to an article for disposal of body wastes such as a urine pad or incontinence pad for woman.

Japanese Patent Application Disclosure No. 1994-178795 describes an absorbent article basically comprising a diaper cover and a rectangular insertion pad. The diaper has a longitudinally front and rear waist regions and a crotch region extending between these two waist regions and is provided along its transversely opposite side edges with a pair of holding flaps biased to rise on the diaper cover. The insertion pad is made of absorbent material and laid between the holding flaps on the upper side of the diaper cover. The pad comprises an absorbent core and a water-pervious sheet covering the absorbent core.

While it is possible for the article disclosed in the Japanese Patent Application Disclosure No. 1994-178795 to prevent an amount of body wastes the pad from leaking by the pair of holding flaps provided on the diaper cover, the pad itself has no function to prevent possibly occurring leakage of body wastes.

SUMMARY OF THE INVENTION

It is an object of this invention to provide an article for disposal of body wastes which improves the containment characteristics thereof.

According to this invention, there is provided an article for disposal of body wastes comprising:

a liquid-pervious inner sheet, a liquid-impervious outer sheet, and a liquid-absorbent core disposed between said inner and outer sheets;

a longitudinally tapered front and rear end sections and a pair of intermediate sections extending between said front and rear sections; and a bottom, a peripheral wall extending upward from a peripheral edge of said bottom and an opening defined by said peripheral wall, said peripheral wall comprising a front peripheral wall portion extending above said front section with a pointed front end, a rear peripheral wall portion extending above said rear section with a pointed rear end and a pair of intermediate peripheral wall portions extending inwardly of said article above said intermediate section so that a distance between the pair of intermediate peripheral wall portions gradually decreases towards said front and rear peripheral wall portions, respectively.

The article for disposal of body wastes according to this invention can be adapted for disposal of urine, feces or menstrual discharge by selecting a position at which the article should be attached to a diaper cover, shorts, pants or the like. Excretion or menstrual discharge having been received by the article through its opening is then absorbed by the core through the inner sheet. The front and rear peripheral wall portions form the pockets and the intermediate peripheral wall portions form barriers so that the article may function to prevent an amount of excretion or menstrual discharge from leaking. The article is adapted to be worn with its front and rear end fitted in a wearer's crotch, because the front and rear ends are tapered.

DETAILED DESCRIPTION OF THE PREFERRED EMBODIMENTS

Details of an article for disposal of body wastes according to this invention will be more fully understood from the description of an absorbent pad attached to the inner side of a diaper cover as one embodiment with reference to the accompanying drawings.

Figure 1:
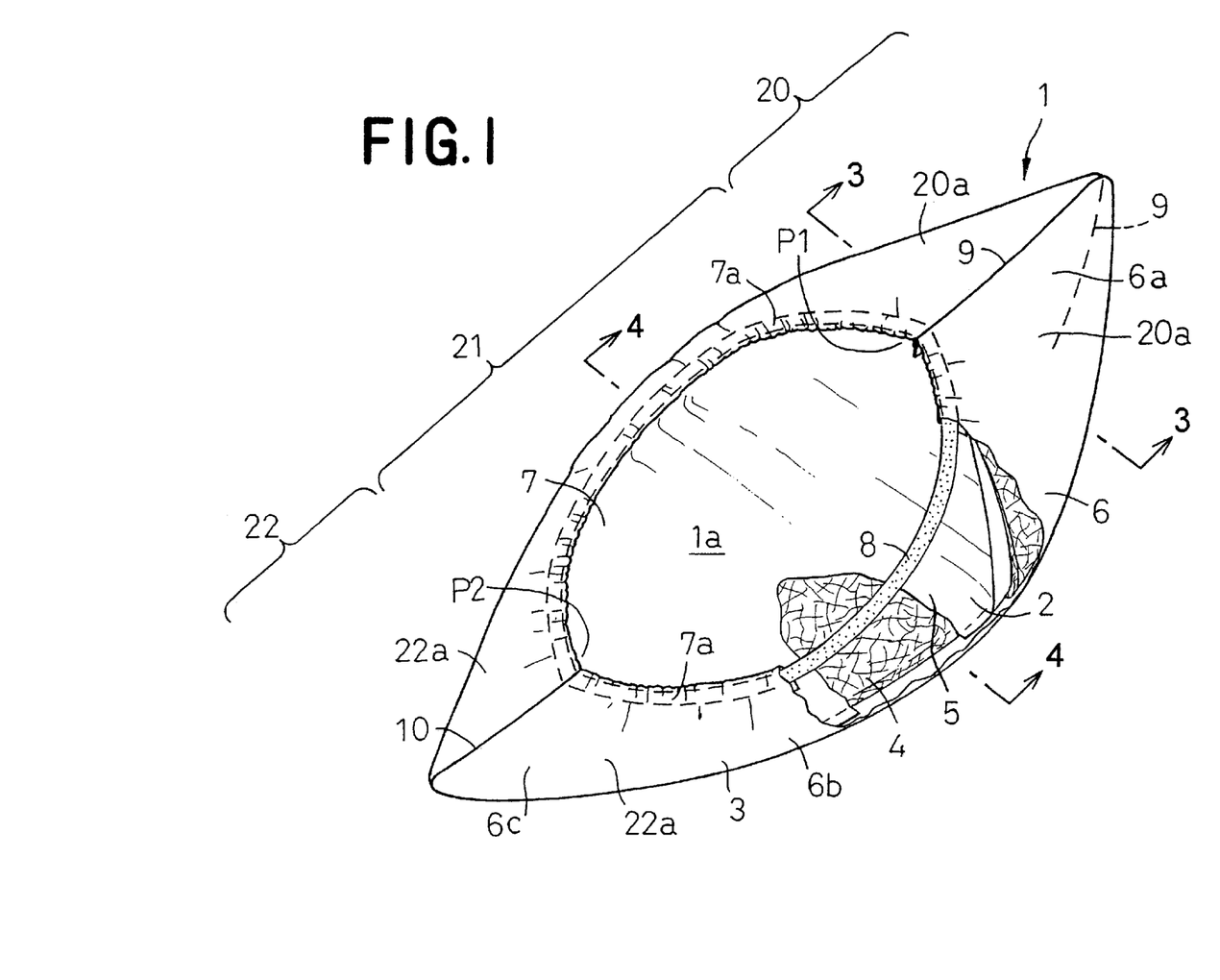
FIG. 1 is a partially cutaway perspective view showing a pad formed by a laminated panel.

FIG. 1 is a partially cutaway perspective view showing an absorbent pad 1 formed by a laminated panel 1a. The panel 1a comprises a liquid-pervious inner sheet 2, a liquid-impervious outer sheet 3 and a liquid-absorbent core 4 disposed between these two sheets 2, 3 and bonded to the inner surface of at least one of the two sheets 2, 3. The pad 1 includes longitudinally tapered front and rear end sections 20, 22, intermediate sections 21 extending between the front and rear end sections 20, 22, and a bottom 5. Aperipheral wall 6 extends upward from a peripheral edge of the bottom 5 and defines an elliptical opening 7.

The peripheral wall 6 comprises a front peripheral wall portion 6a extending above the front end section 20 with its pointed front end extending upwardly of the pad 1, a rear peripheral wall portion 6c extending above the rear end section 22 with its pointed rear end, and a pair of intermediate peripheral wall portions 6b extending so as to be curved inwardly of the pad 1 above its intermediate sections 21. The rear peripheral wall portion 6c has a transverse dimension smaller than that of the front peripheral wall portion 6a. The pair of intermediate peripheral wall portions 6b are spaced from each other by a dimension progressively decreasing toward the front and rear peripheral wall portions 6a, 6c. The peripheral wall 6 is provided along a peripheral edge 7a of the opening 7 with film-like elastic members 8 secured under tension thereto.

The front peripheral wall portion 6a cooperates with the bottom 5 to form a pocket P1 extending forward longitudinally of the pad 1 and the rear peripheral wall portion 6c cooperates with the bottom 5 to form a pocket P2 extending rearward longitudinally of the pad 1.

Figure 2:
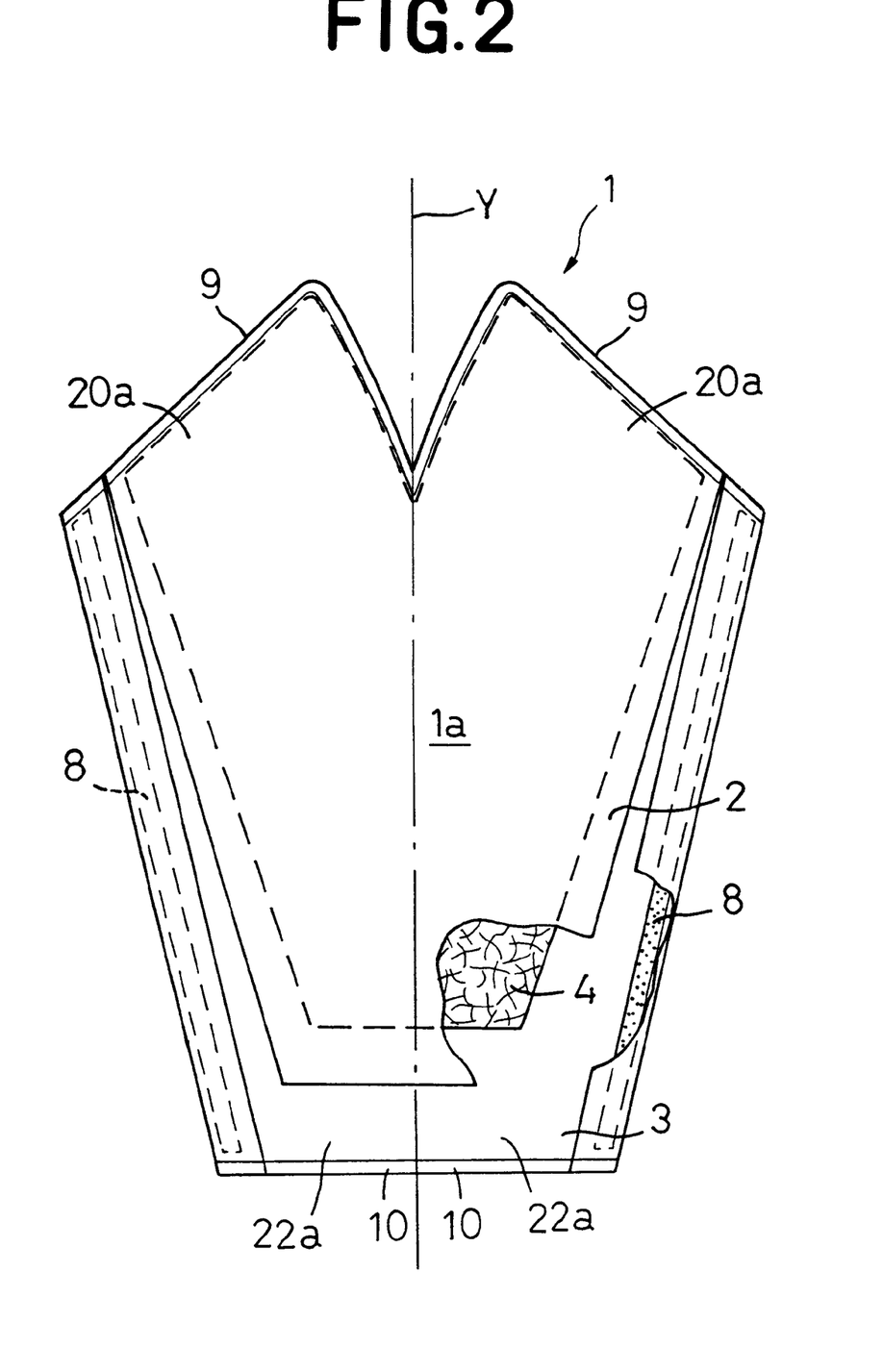
FIG. 2 is a partially cutaway plan view showing the panel of FIG. 1 as before its peripheral wall is formed.

FIG. 2 is a partially cutaway plan view showing the pad 1 of FIG. 1 as before the peripheral wall 6 is formed. The front end section 20 of the pad 1 has, on both sides of a center line Y bisecting a transverse dimension of the pad 1, a pair of joining edges 9 which extend forward longitudinally of the pad 1 to form convexities, respectively. Specifically, each of the joining edges 9 extends forward and progressively away from the center line Y toward the front end of the pad 1 and then turns at the front end to extend rearward and progressively away from the center line Y. The rear end section 22 of the pad 1 has, on both sides of said center line Y, a pair of substantially rectilinear joining edges 10 extending transversely of the pad 1. In a state illustrated in FIG. 2, the elastic members 8 extend along transversely opposite side edges of the pad 1, respectively.

The front peripheral wall portion 6a comprises respective portions of the inner sheet 2, the outer sheet 3 and the core 4 disposed between the two sheets 2, 3. The rear peripheral wall portion 6c and the intermediate peripheral wall portions 6b comprise a portion of the inner sheet 2 extending slightly beyond a peripheral edge of the core 4 and a portion of the outer sheet 3 extending beyond a peripheral edge of the inner sheet 2.

The front peripheral wall portion 6a is formed by pulling a pair of divisions 20a of the front end section 20 lying on both sides of the center line Y nearer to each other and joined along the joining edges 9 to each other on the center line Y. The rear peripheral wall portion 6c is formed by pulling a pair of divisions 22a of the rear end section 22 lying on both sides of the center line Y nearer to each other and joined along the joining edges 10 to each other on the center line Y.

With the elastic members 8 being relaxed in the finished pad 1, the peripheral wall 6 is formed along the edge 7 of the opening 7 with gathers. At the same time, the front and rear end sections 20, 22 are pulled inward longitudinally of the pad 1 so that the front end of the front peripheral wall portion 6a and the rear end of the rear peripheral wall portion 6c are raised. Consequently, the front and rear peripheral wall portions 6a, 6c exhibit respective rising gradients.

Figure 3:
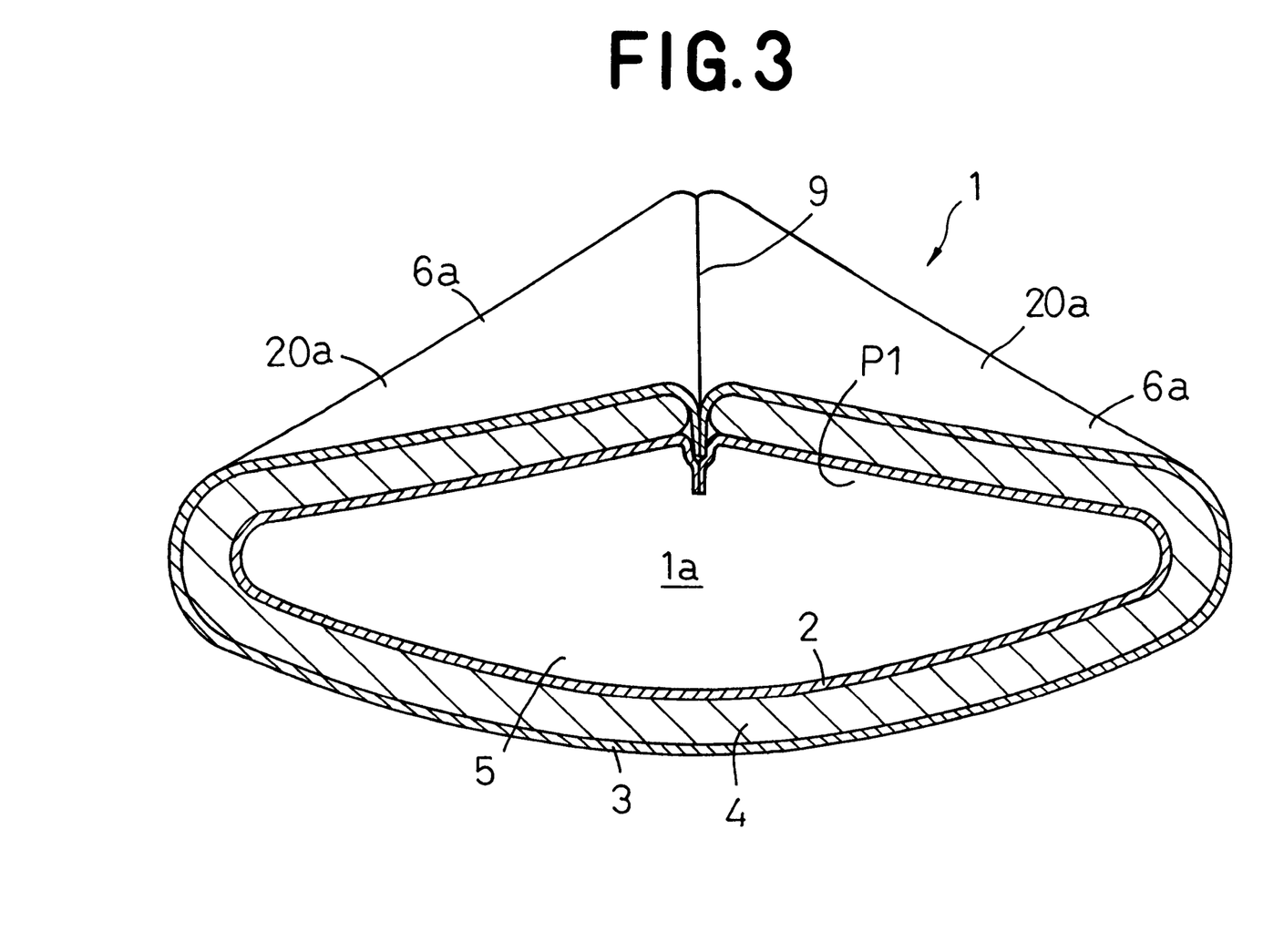
FIG. 3 is a sectional view taken along line A—A in FIG. 1.
Figure 4:
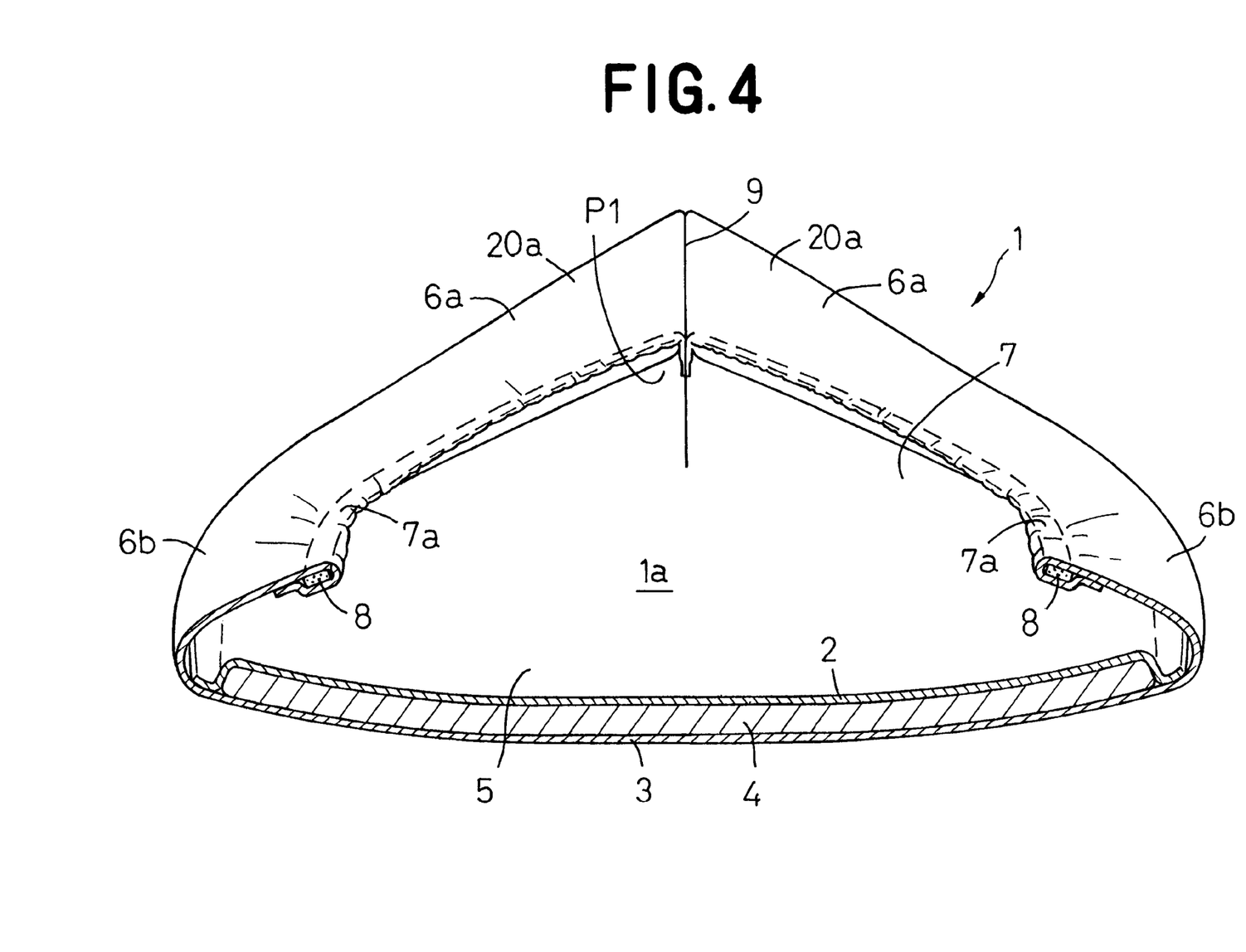
FIG. 4 is a sectional view taken along line B—B in FIG. 1.

FIG. 3 is a sectional view taken along line A—A in FIG. 1 and FIG. 4 is a sectional view taken along line B—B in FIG. 1. The front peripheral wall portion 6a of the pad 1 extends obliquely upward from the bottom 5 toward the joining edges 9. Along these joining edges 9, transversely opposite side edges of the inner sheet 2 are folded inwardly of the pad 1 and joined to each other. Transversely opposite side edges of the outer sheet 3 extending outward beyond the side edges of the inner sheet 2 are folded inwardly of the pad 1 and joined to each other along the joining edges 9.

In the intermediate peripheral wall portions 6b, the transversely opposite side edges of the inner sheet 2 extend outward slightly beyond transversely opposite side edges of the core 4 and the transversely opposite side edges of the outer sheet 3 extend largely outward from the side edges of the inner sheet 2. These extensions of the outer sheet 3 have their upper ends folded inwardly of the pad 1 to wrap the elastic members 8.

Figure 5:
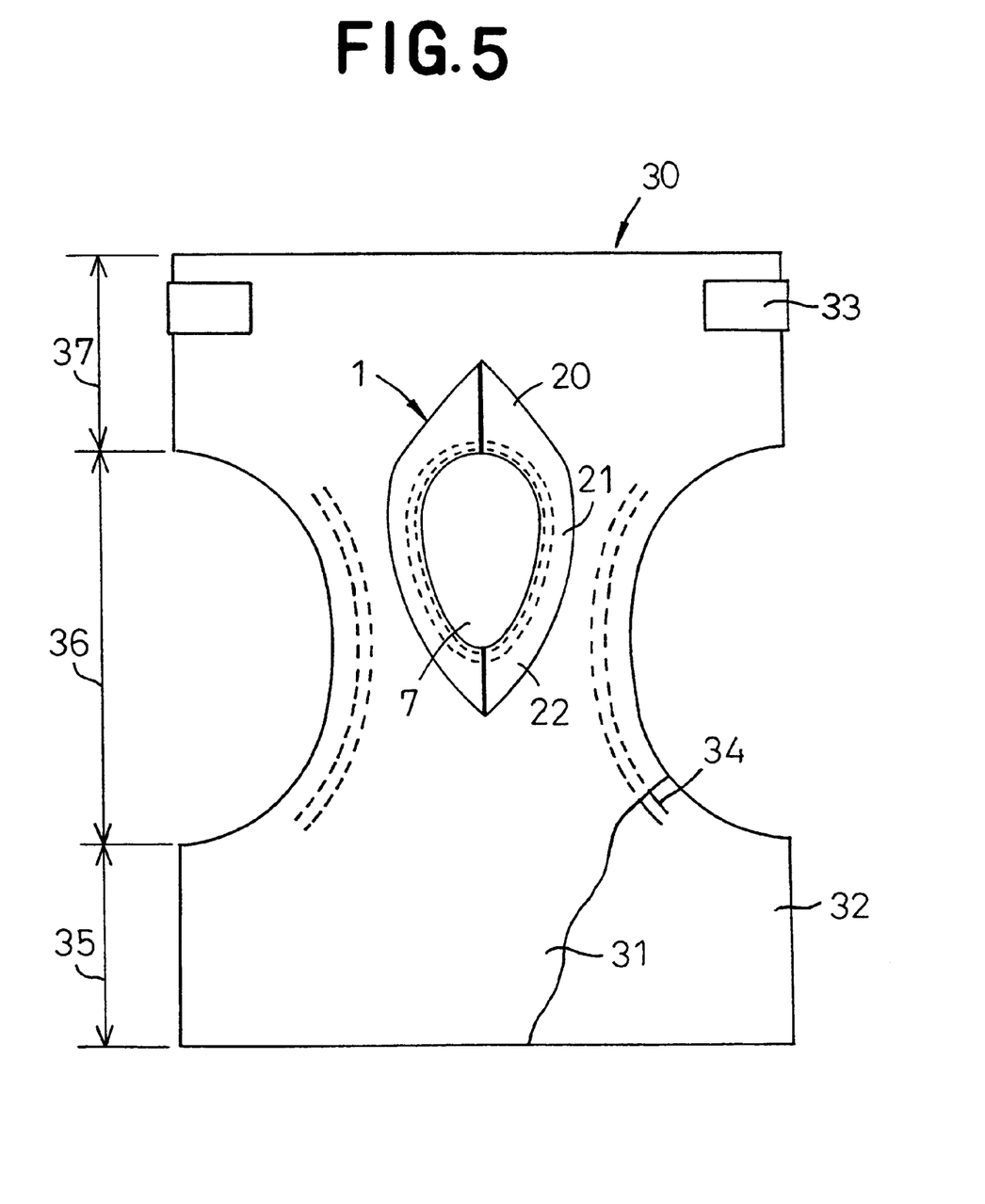
FIG. 5 is a partially cutaway plan view showing the panel attached to a diaper.

FIG. 5 is a partially cutaway plan view showing the pad 1 attached to a diaper cover 30. The diaper cover 30 comprises an hourglass-shaped laminate including an inner sheet 31 made of a plastic film and an outer sheet 32 made of a nonwoven fabric. The cover 30 has longitudinally front and rear waist regions 35, 37 and a crotch region 36 extending between these two waist regions 35, 37. The crotch region 36 has its transversely opposite side edges curved inward.

The crotch region 36 is provided along the side edges with elastic members 34 secured under tension to the inner surface of at least one of the inner and outer sheets 31, 32. The cover 30 is applied on its inner surface with suitable adhesive agent (not shown) by means of which the pad 1 is detachably fastened to the cover 30. The position at which the pad 1 is fastened to the cover 30 is selective depending on whether the pad 1 is used as an urine pad or sanitary napkin pad.

The cover 30 is provided on transversely opposite side edges of the rear waist region 37 with a pair of tape fasteners 33. As in the case of conventional disposable diapers, these tape fasteners 33 enable an assembly of the pad 1 and the cover 30 to be put on a user's body so that the user's anus may be positioned substantially at a center of the opening 7 of the pad 1.

With the pad 1 being used in this manner, excretion is discharged in the opening 7 and it is not concerned that the cover 30 might be soiled with excretion. Disposal of excretion can be easily done merely by holding the pad 1 substantially smaller than the cover 30. The pad 1 is preferably attached to the cover 30 so that the rear peripheral wall portion 6c narrower than the front peripheral wall portion 6a may be smoothly received by a user's crotch without any feeling of discomfort as the cover 30 is put on the user's body positioned. On the other hand, the front peripheral wall portion 6a having a width larger than the rear peripheral wall portion 6c can receive and hold therein a large amount of excretion. Both the front and rear end sections 20, 22 of the pad 1 have respective rising gradients with respect to the pad 1 and therefore can follow a deformation of the cover 30 as the latter is curved with its inner surface inside.

Figure 6:
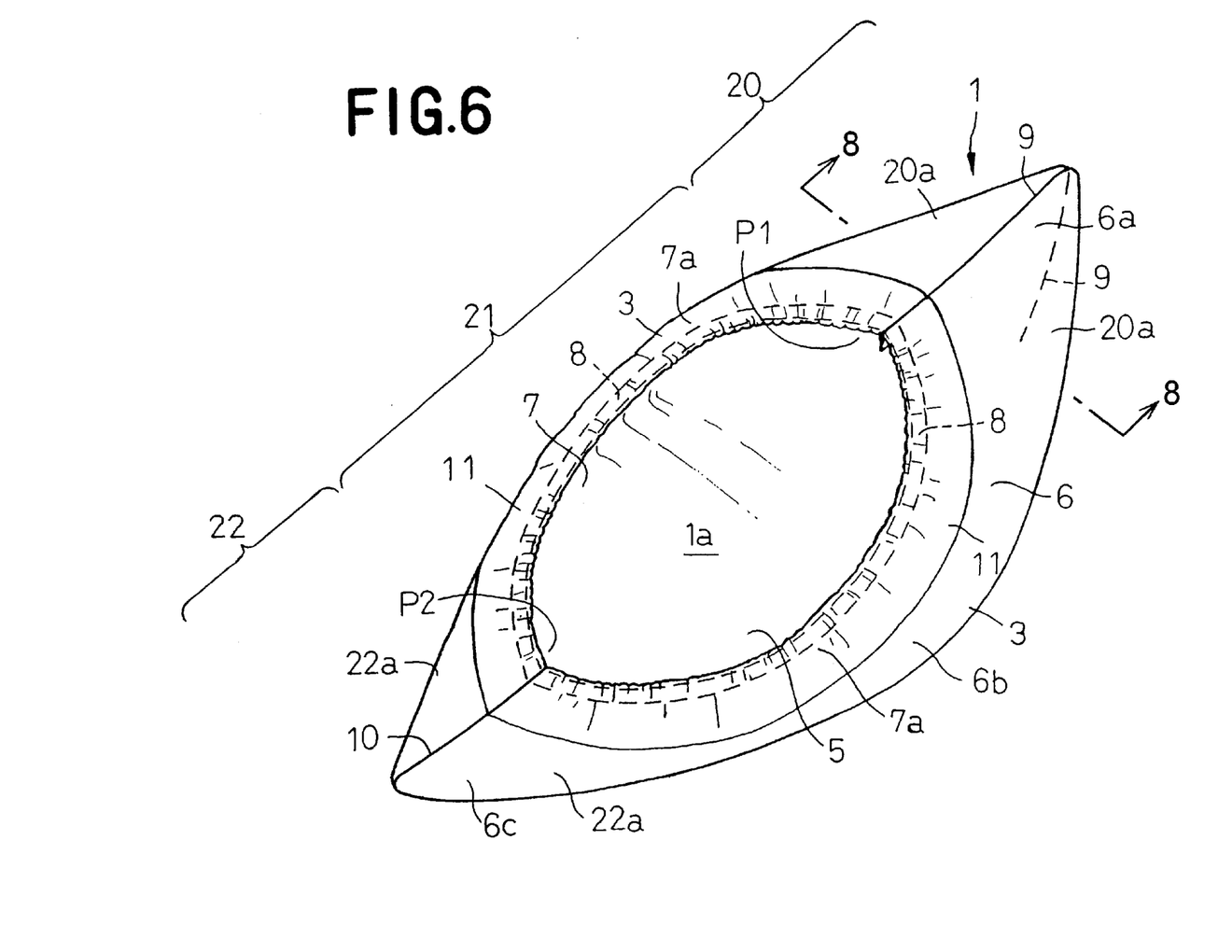
FIG. 6 is a view similar to FIG. 1 showing another embodiment of the panel.

FIG. 6 is a view similar to FIG. 1 showing another embodiment of the pad 1. The pad 1 also comprises a laminated panel 1a formed by the inner sheet 2, the outer sheet 3 and the core 4 disposed between these two sheets 2, 3. The pad 1 of FIG. 6 is similar to the pad 1 of FIG. 1 also in the other aspects. Specifically, the pad 1 of FIG. 6 also has the longitudinally front and rear end sections 20, 22 and the pair of intermediate sections 21. The peripheral wall 6 also is of the same type as the peripheral wall 6 in the pad 1 of FIG. 1. However, the opening peripheral edge 7a of the pad 1 shown in FIG. 6 comprises ribbon-like hem members 11 provided separately of the side edges of the inner sheet 2 as well as the side edges of the outer sheet 3.

Figure 7:
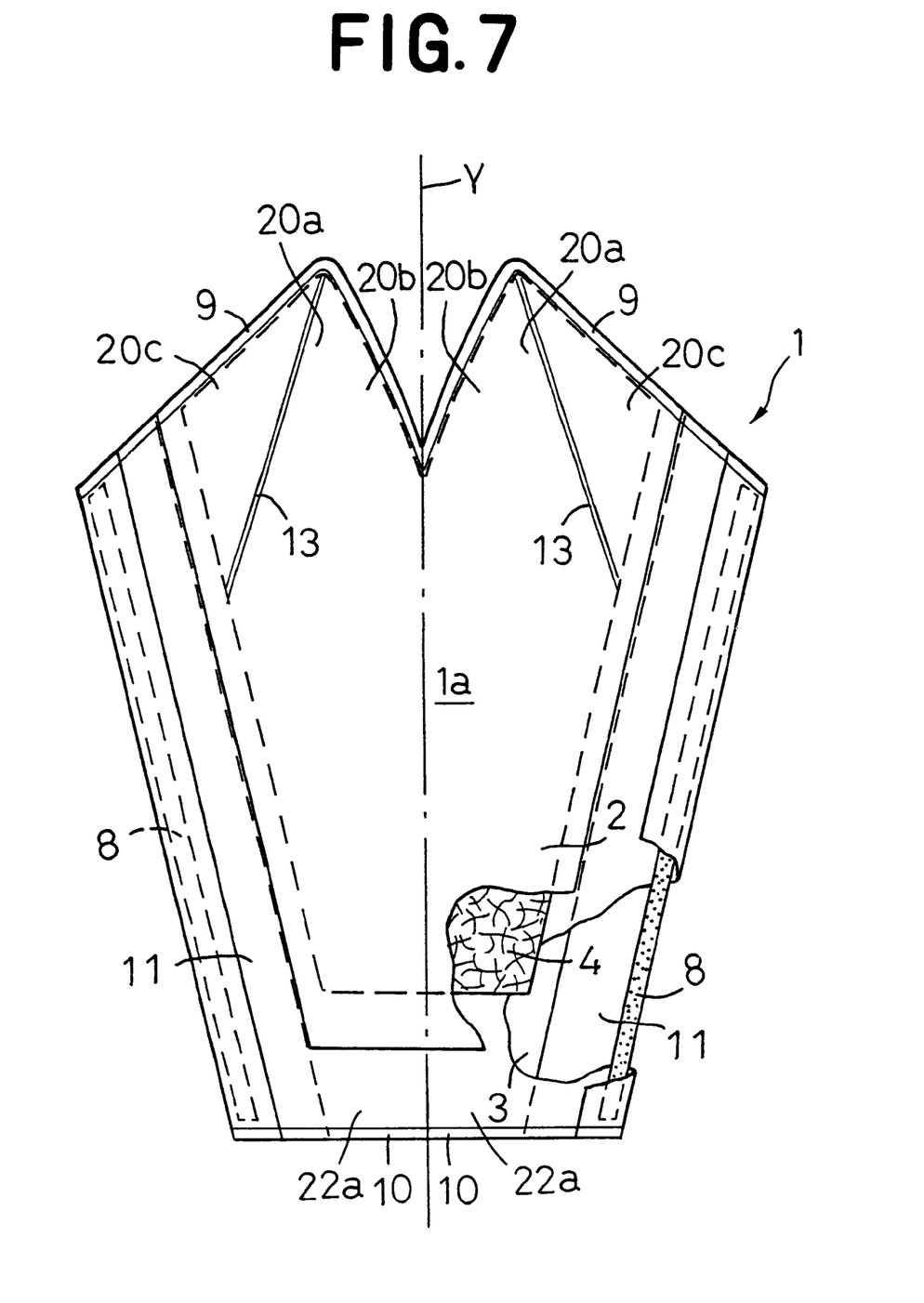
FIG. 7 is a view similar to FIG. 2 showing the panel of FIG. 6.

FIG. 7 is a view similar to FIG. 2 showing the pad of FIG. 6. The peripheral edge of the pad 1 except the joining edges 9 comprises the portion of the inner sheet 2 and the outer sheet 3 extending outward beyond the periphery of the core 4, and the hem members 11 disposed between these portions and joined to at least one of these portions. The hem members 11 are longitudinally provided with film-like elastic members 12 secured under tension thereto. In the pad 1 completely assembled along the joining edges 9 as well as along the joining edges 10, the hem members 11 partially constitute the edge 7a of the opening 7 and the intermediate peripheral wall portions 6b.

The front peripheral wall portion 6a of the pad 1 is formed with a pair of folds 13 extending longitudinally to divide the respective divisions 20a of the front end section 20 in two. Specifically, the divisions 20a are further divided by the respective folds 13 into a pair of inner regions 20b and a pair of outer regions 20c. The folds 13 are formed by compressing the core 4 together with the inner sheet 2 and function as guides facilitating the outer regions 20c to be easily folded with respect to the inner regions 20b.

Figure 8:
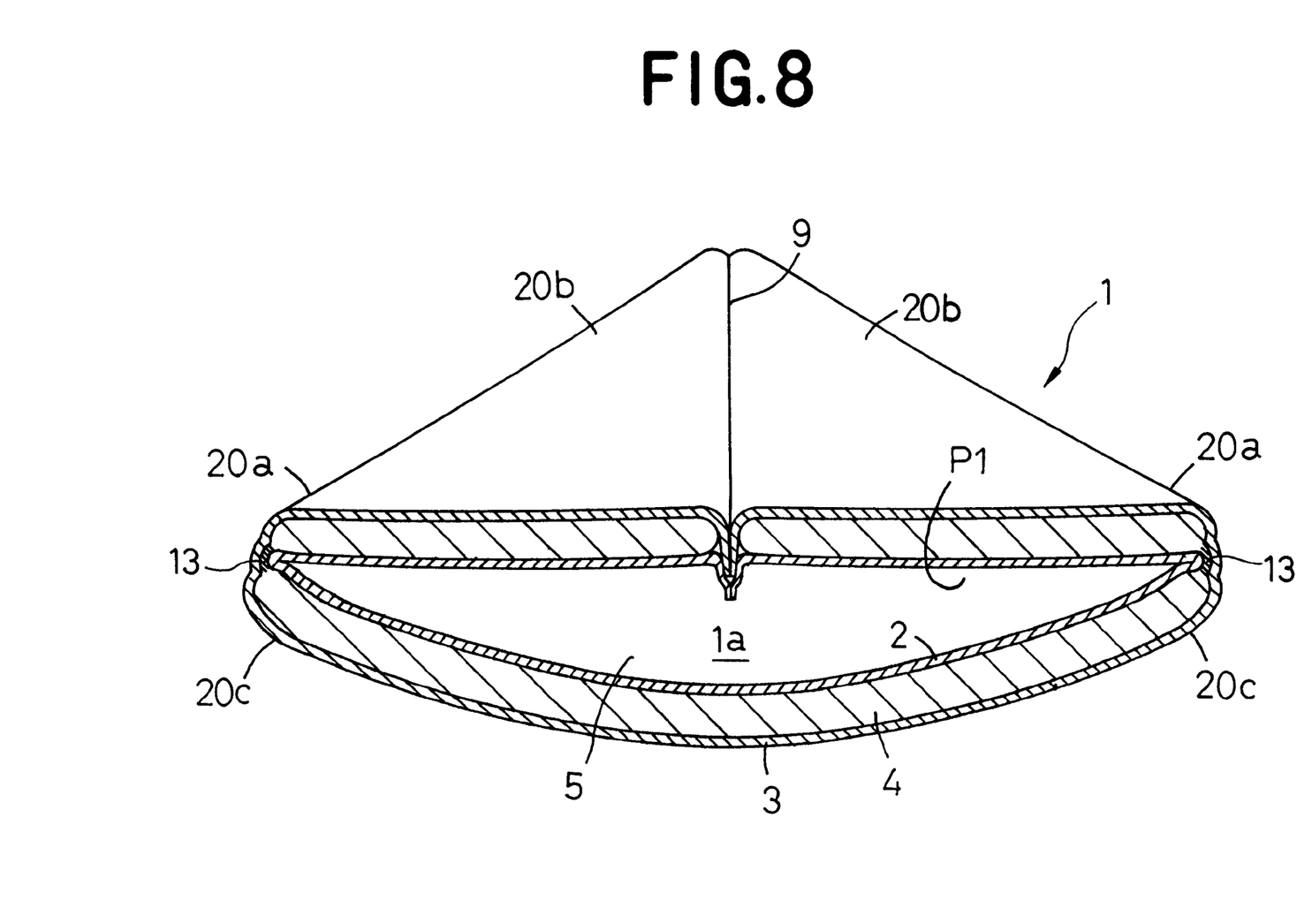
FIG. 8 is a sectional view taken along line C—C in FIG. 6.

FIG. 8 is a sectional view taken along line C—C in FIG. 6. As shown, the outer regions 20c of the front peripheral wall portion 6a have been folded along the respective folds 13 and present a substantially smooth surface destined to come in contact with a user's skin. Accordingly, it is not concerned that use of the pad might give the user a feeling of discomfort due to use of the pad 1.

It is possible without departing from the scope of this invention to arrange the front peripheral wall portion 6a so that the folds 13 comprise the inner sheet 2 and the outer sheet 3 and the inner regions 20b as well as the outer regions 20c of the respective divisions 20a contain the core 4. The respective folds 13 containing no portion of the core 4 are not affected by a rigidity of the core 4 and therefore facilitate the outer regions to be folded inwardly of the pad 1.

The inner sheet 2 may be made of a liquid-pervious sheet such as a nonwoven fabric or porous plastic film, preferably a liquid-pervious but hydrophobic sheet. The outer sheet 3 may be made of a liquid-impervious plastic film, a laminate of plastic film and hydrophobic nonwoven fabric, or preferably a breathable and liquid-impervious sheet.

The hem members 11 may be made of a breathable and liquid-impervious nonwoven fabric or breathable, liquid-impervious and elastic nonwoven fabric. If the elastic nonwoven fabric is used as stock material for the hem members 11, these sheet-like members 11 may be joined under longitudinal tension to the pad 1 to eliminate use of the elastic members 12. A feeling of discomfort due to the hem members 11 coming in contact with a user's skin may be effectively alleviated by using the hem members 11 made of a nonwoven fabric having a rigidity lower than that of the outer sheet 3.

The nonwoven fabric used as the stock material may be selected from a group including spun lace, needle punch, melt blown, thermal bond, spun bond and chemical bond types. A basis weight is 15~80 g/m$^2$, preferably 20~60 g/m$^2$. Component fiber may be selected from a group including polyolefine, polyester, polyamide fibers, and a conjugated fiber of polyethylene/polypropylene or polyester.

The core 4 is formed by compressing a mixture of fluff pulp and superabsorptive hydrogel particles and then covering it entirely with a water-pervious sheet such as tissue paper. Joining of the sheets and the elastic members may be achieved using adhesive agent such as hot melt adhesive, glue or heat-sealing technique.

This invention is not limited to use in combination with the diaper cover but can be used as the independent article for disposal of excretion by attaching the article directly to shorts or pants worn by a user.

What is claimed is:

1. An article for disposal of body wastes comprising:

a liquid-pervious inner sheet, a liquid-impervious outer sheet, and a liquid-absorbent core disposed between said inner and outer sheets;

a longitudinally tapered front and rear end sections and a pair of intermediate sections extending between said front and rear sections; and a bottom, a peripheral wall extending upward from a peripheral edge of said bottom and an opening defined by said peripheral wall, said peripheral wall comprising a front peripheral wall portion extending above said front section with a pointed front end, a rear peripheral wall portion extending above said rear section with a pointed rear end and a pair of intermediate peripheral wall portions extending inwardly of said article above said intermediate section so that a distance between the pair of intermediate peripheral wall portions gradually decreases towards said front and rear peripheral wall portions, respectively.

2. The article according to claim 1, wherein said rear peripheral wall portion has a transverse dimension smaller than a transverse dimension of said front peripheral wall portion.

3. The article according to claim 1, wherein said pointed front end of said front peripheral wall portion extend upward of said article.

4. The article according to claim 1, wherein said front peripheral wall portion is formed by pulling divisions of said front end section lying both sides of a longitudinal center line of said panel nearer to each other toward said center line until a pair of first bonding edges convexly extending toward their longitudinally front ends thereof are joined together, respectively, on said center line; and said rear peripheral wall portion is formed by pulling divisions of said rear end section lying on both sides of said center line nearer to each other toward said center line until a pair of second bonding edges extending transversely on both sides of said center line are joined together on said center line.

5. The article according to claim 1, wherein at least one of said front peripheral wall portion and said rear peripheral wall portion comprises a portion of said inner sheet, a portion of said outer sheet and a portion of said core disposed between said inner and outer sheets and said intermediate peripheral wall portions comprise at least a portion of said outer sheet.

6. The article according to claim 1, wherein said front peripheral wall portion is provided along a peripheral edge of said opening with a hem member joined to at least one of said portion of said inner sheet and said portion of said outer sheet.

7. The article according to claim 1, wherein said peripheral wall has an elastic stretchability along said peripheral edge of said opening.

8. The article according to claim 1, wherein said front peripheral wall portion includes a pair of folds each longitudinally extending to divide a transverse dimension of the associated division in two so that the respective divisions of said front peripheral wall portion are further divided into outer regions lying on transversely outer sides of the respective folds and inner regions lying on transversely inner sides of the respective folds.

9. The article according to claim 1, wherein said article is an absorbent pad adapted to be attached to an inner side of a diaper cover.

* * * * *